United States Patent
Smith et al.

(10) Patent No.: US 9,157,883 B2
(45) Date of Patent: Oct. 13, 2015

(54) METHODS AND SYSTEMS TO DETERMINE FILL DIRECTION AND FILL ERROR IN ANALYTE MEASUREMENTS

(71) Applicant: LifeScan Scotland Limited, Inverness-shire (GB)

(72) Inventors: Antony Smith, Dingwall (GB); Neil Whitehead, Dingwall (GB); Lynsey Whyte, Newtonmore (GB)

(73) Assignee: LifeScan Scotland Limited, Inverness (GB)

(*) Notice: Subject to any disclaimer, the term of this patent is extended or adjusted under 35 U.S.C. 154(b) by 405 days.

(21) Appl. No.: 13/788,409

(22) Filed: Mar. 7, 2013

(65) Prior Publication Data

US 2014/0251833 A1    Sep. 11, 2014

(51) Int. Cl.
*G01N 27/327* (2006.01)
*B01L 3/00* (2006.01)

(52) U.S. Cl.
CPC ....... *G01N 27/3274* (2013.01); *B01L 3/502715* (2013.01); *B01L 2200/04* (2013.01); *B01L 2200/10* (2013.01); *B01L 2200/143* (2013.01); *B01L 2300/0825* (2013.01); *B01L 2400/0406* (2013.01); *G01N 27/3273* (2013.01)

(58) Field of Classification Search
CPC .................................. G01N 27/3271–27/3274
See application file for complete search history.

(56) References Cited

U.S. PATENT DOCUMENTS

| | | |
|---|---|---|
| 5,708,247 A | 1/1998 | McAleer et al. |
| 5,951,836 A | 9/1999 | McAleer et al. |
| 6,241,862 B1 | 6/2001 | McAleer et al. |
| 6,284,125 B1 | 9/2001 | Hodges et al. |
| 6,733,655 B1 | 5/2004 | Davies et al. |
| 6,743,635 B2 * | 6/2004 | Neel et al. ............ 436/95 |
| 2005/0023152 A1 * | 2/2005 | Surridge et al. ........ 205/775 |
| 2008/0211813 A1 | 9/2008 | Jamwal et al. |
| 2009/0014328 A1 | 1/2009 | Feldman et al. |
| 2011/0297557 A1 | 12/2011 | Wu et al. |

FOREIGN PATENT DOCUMENTS

| | | |
|---|---|---|
| KR | 10-0757297 B1 | 9/2007 |
| WO | 2006040200 A1 | 4/2006 |
| WO | 2013098563 A1 | 7/2013 |
| WO | 2013098564 A1 | 7/2013 |
| WO | 2013098565 A1 | 7/2013 |

OTHER PUBLICATIONS

International Search Report and Written Opinion issued in corresponding International Application No. PCT/EP2014/054322, mailed May 27, 2014; 15 pages.

* cited by examiner

*Primary Examiner* — Alexander Noguerola

(57) ABSTRACT

Various embodiments for methods and systems that allow for detecting of a direction in which a sample is flowing towards a plurality of electrodes and detecting a fill error of an electrochemical test strip.

19 Claims, 10 Drawing Sheets

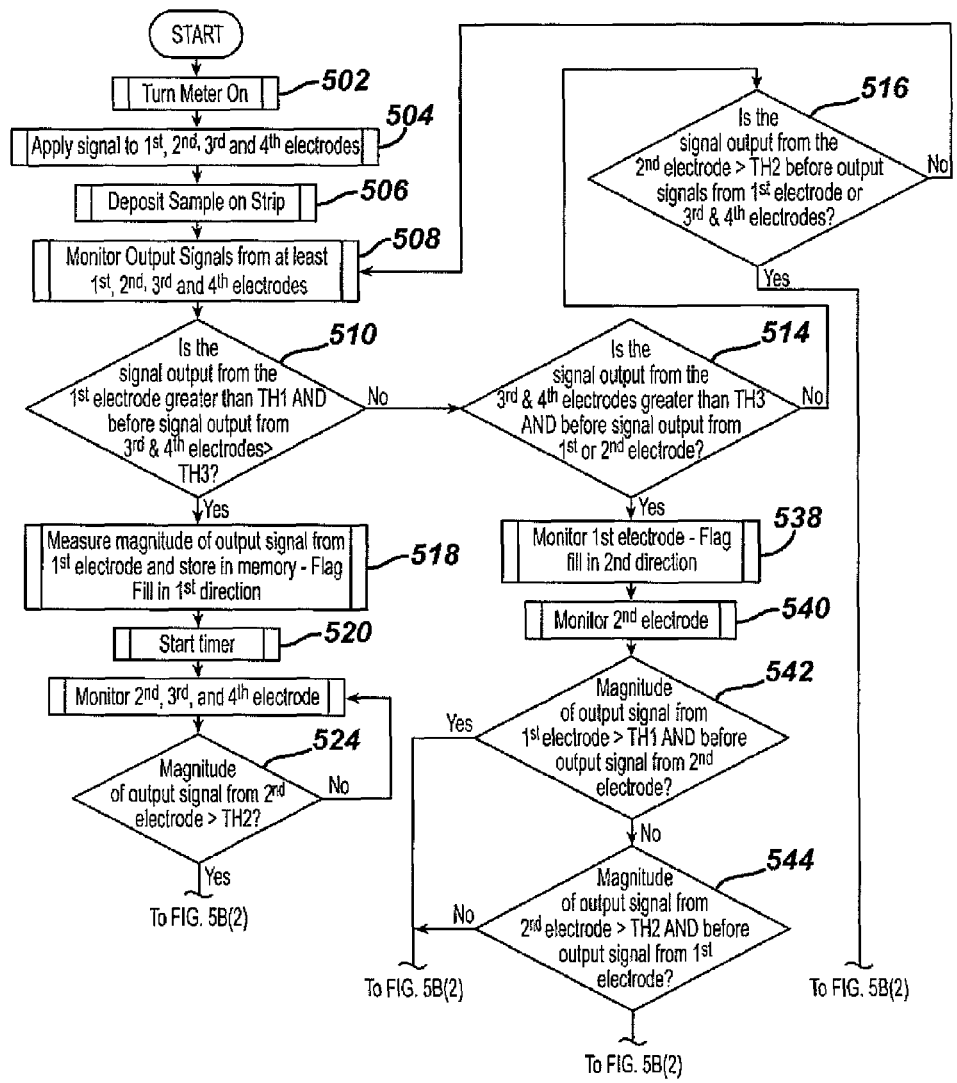
FIG. 5B(1)

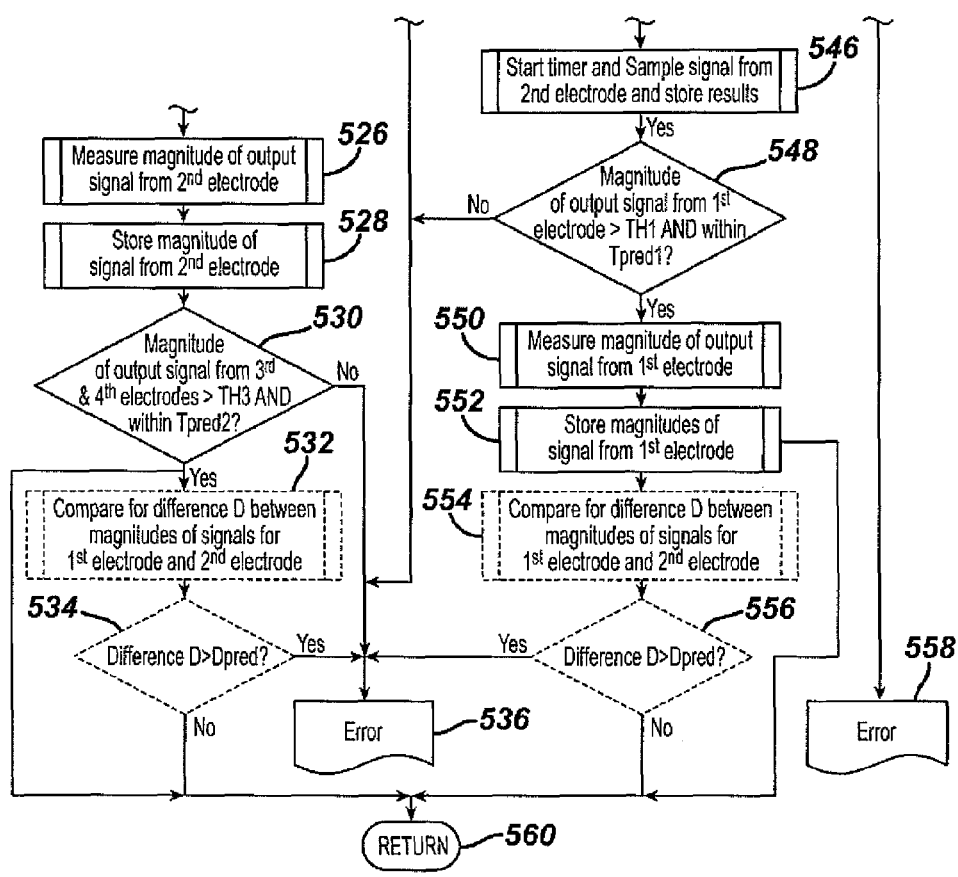
FIG. 5B(2)

METHODS AND SYSTEMS TO DETERMINE FILL DIRECTION AND FILL ERROR IN ANALYTE MEASUREMENTS

BACKGROUND

Electrochemical glucose test strips, such as those used in the OneTouch® Ultra® whole blood testing kit, which is available from LifeScan, Inc., are designed to measure the concentration of glucose in a physiological fluid sample from patients with diabetes. The measurement of glucose can be based on the selective oxidation of glucose by the enzyme glucose oxidase (GO). The reactions that can occur in a glucose test strip are summarized below in Equations 1 and 2.

$$\text{Glucose} + GO_{(ox)} \rightarrow \text{Gluconic Acid} + GO_{(red)} \quad \text{Eq. 1}$$

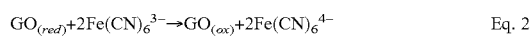

$$GO_{(red)} + 2Fe(CN)_6^{3-} \rightarrow GO_{(ox)} + 2Fe(CN)_6^{4-} \quad \text{Eq. 2}$$

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ (referred to as either the oxidized mediator or ferricyanide) as illustrated in Equation 2. During the re-generation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test signal in the form of potential applied between two electrodes, a test signal in the form of a current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test output signal generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test output signal, resulting from the re-oxidation of reduced mediator, and glucose concentration. In particular, the transfer of electrons across the electrical interface results in the flow of a test output signal (2 moles of electrons for every mole of glucose that is oxidized). The test output signal resulting from the introduction of glucose can, therefore, be referred to as a glucose output signal.

SUMMARY OF THE DISCLOSURE

Applicants have discovered that in test strips where there is more than one sample fill opening, there can be a mismatch as to when to start sampling the output signals depending on which opening was utilized or if the sample was provided concurrently in more than one openings. Applicants have also discovered that where the test strip includes other electrodes for sensing a physical characteristic (e.g., hematocrit, density, viscosity, or temperature and the like) of the sample, these additional electrodes can also be utilized to determine a fill direction or fill error.

Accordingly, we have provided various embodiments of a technique to allow for determining a sample fill error in an analyte test strip having at least two electrodes spaced apart along a fill passage disposed on a substrate that extends from at least a first opening to a second opening.

In one aspect, we have provided a method to ameliorate or obviate the problems discovered by us and to attain a new technique heretofore not available in the art. In particular, our method can be achieved by: applying a signal to first and second electrodes of the at least two electrodes; depositing a fluid sample into one of the first and second openings; monitoring the first and second electrodes for output signals indicative of an electrochemical reaction; and in the event the first electrode or the second electrode outputs a signal before the other of the first and second electrodes then monitoring the other of the first and second electrodes for a signal output within a predetermined time period else reporting a fill error when the signal output of the other electrode is after the predetermined time period.

In this aspect, the method may include measuring a signal from the second electrode during a sampling interval of a test sequence time; comparing a magnitude of the signal from the second electrode with magnitude of the signal from the first electrode; and reporting an error if the magnitude of the signal from the second electrode is different by a predetermined percent differential from the magnitude of the signal from the first electrode otherwise summing the magnitudes of the signals and calculating an analyte concentration based on the summed magnitudes.

Alternatively, the method may include measuring a signal from the first electrode during a sampling interval of a test sequence time; comparing a magnitude of the signal from the first electrode with magnitude of the signal from the second electrode; and reporting an error if the magnitude of the signal from the first electrode is different by a predetermined percent differential from the magnitude of the signal from the second electrode otherwise summing the magnitudes of the signals and calculating an analyte concentration based on the summed magnitudes of the signals. Alternatively, the measured signals can be an averaged of the values from each of the electrodes. In yet another alternative, the signal can be just one value measured from one electrode. It is noted that the predetermined percent differential comprises any value from about 30% to 10%.

In yet another aspect, we have also provided a method of determining a sample fill error in an analyte test strip. The test strip may have first, second, fourth, and fifth electrodes spaced apart along a fill passage disposed on a substrate that extends from at least a first opening to a second opening. The method can be achieved by: applying a signal to the first, second, third, and fourth electrodes; depositing a fluid sample into one of the first and second openings; monitoring the first through fourth electrodes for a signal output representative of a deposition of fluid sample onto the test strip; in the event the first electrode outputs a signal greater than a first threshold before one of the third or fourth electrodes outputs a signal greater than a second threshold then: sampling the signal from the first electrode and measuring the second, third and fourth electrodes for a signal output from the second electrode greater than the first threshold and a signal output from at least one of the third and fourth electrodes greater than the second threshold within a first predetermined time period otherwise reporting a fill error when the signal output from at least one of the third and fourth electrodes is after the first predetermined time period.

In yet a further aspect, we have devised a method of determining a sample fill direction for an analyte test strip that has at least two electrodes spaced apart along a fill passage disposed on a substrate that extends from at least a first opening to a second opening. The method can be achieved by: applying a signal to first and second electrodes of the at least two electrodes; depositing a fluid sample into one of the first and second openings; monitoring the first and second electrodes for output signals indicative of an electrochemical reaction; in the event the first electrode outputs a signal greater than a first predetermined threshold before the second electrodes, storing in memory an indication that a direction of the movement of the sample is in a first direction; and in the event the second electrode outputs a signal greater than a second predetermined threshold before the first electrode, storing in memory an indication that a direction of the movement of the sample is in a second direction.

In another aspect, we devised a method of determining a sample fill direction for an analyte test strip that has at least first, second, fourth, and fifth electrodes spaced apart along a fill passage disposed on a substrate that extends from at least a first opening to a second opening such that a sample can move from the first opening toward the second opening or from the second opening toward the first opening. The method can be achieved by: applying a signal to the first, second, third, and fourth electrodes; depositing a fluid sample into one of the first and second openings; monitoring the first through fourth electrodes for a signal output representative of a deposition of fluid sample onto the test strip; in the event the first electrode outputs a signal greater than a first threshold before one of the third or fourth electrodes outputs a signal greater than a third threshold then: selecting a first measurement based on output signals from each of the first and second electrodes before a second measurement based on output signals from the third and fourth electrodes; and in the event the third and fourth electrodes output a signal greater than a second threshold and before any output signal from one of the first and second electrodes then: selecting the second measurement based on output signals from the third and fourth electrodes before the first measurement based on output signals from each of the first and second electrodes.

In another aspect, we have devised a system that includes a test strip and a test meter. The test strip includes: a substrate having at least first, second third, fourth, and fifth electrodes disposed in a passage extending between a first opening and a second opening to permit fluid sample to flow into one or more of the openings. The test meter includes: a housing; a test strip port connector configured to connect to the respective electrode connectors of the test strip; and a microprocessor in electrical communication with the test strip port connector to apply electrical signals or sense electrical signals from the plurality of electrodes during a test sequence, wherein the microprocessor is configured to: (a) apply a signal to the first, second, third, and fourth electrodes; (b) monitor the first through fourth electrodes for a signal output representative of a deposition of fluid sample onto the test strip; (c) in the event the first electrode outputs a signal greater than a first threshold before one of the third or fourth electrodes outputs a signal greater than a second threshold then: (i) sample the signal from the first electrode and (ii) measure the second, third and fourth electrodes for a signal output from the second electrode greater than the first threshold and a signal output from at least one of the third and fourth electrodes greater than the second threshold within a first predetermined time period otherwise report a fill error when the signal output from at least one of the third and fourth electrodes is after the first predetermined time period; (d) in the event one of or both of the third and fourth electrodes output a signal greater than the third threshold before one of the first and second electrodes outputs a signal greater than the first threshold then: (i) determine whether the first electrode outputs a signal greater than the first threshold before the second electrode and report an error if true, (ii) otherwise determine whether the second electrode outputs a signal greater than the first threshold before the first electrode and if true monitor the first electrode to determine whether the first electrode outputs a signal greater than the first threshold within a second predetermined time period, and (e) in the event the first electrode fails to outputs a signal greater than the first threshold within the second time period, report an error.

In any of the aspects described earlier, the following features may also be utilized in various combinations with these previously disclosed aspects. For example, the method may include the steps of: in the event one of or both of the third and fourth electrodes output a signal greater than the third threshold before one of the first and second electrodes outputs a signal greater than the first threshold then: determining whether the first electrode outputs a signal greater than the first threshold before the second electrode and reporting an error if true, otherwise determining whether the second electrode outputs a signal greater than the first threshold before the first electrode and if true monitoring the first electrode to determine whether the first electrode outputs a signal greater than the first threshold within a second predetermined time period, and in the event the first electrode fails to outputs a signal greater than the first threshold within the second time period, reporting an error. As another example, the method may include detecting whether a signal output from the second electrode is greater than a third threshold before a signal output from any one of the first, third and fourth electrodes and if the detecting is true, reporting an error; the measuring of the second, third and fourth electrodes further comprises comparing a magnitude of the signal from the second electrode with the first electrode and outputting an error whenever a difference in magnitude between the signal of the first electrode and the signal of the second electrode is greater than a predetermined percentage; comparing a magnitude of the signal from the second electrode with the first electrode and outputting an error whenever a difference in magnitude between the signal of the first electrode and the signal of the second electrode is greater than a predetermined percentage; the predetermined percent differential comprises any value from about 30% to 10%; the analyte test strip further includes reference electrode dispose proximate the first and second electrodes; a fifth electrode connected to one of the first, second, third, fourth or reference electrodes; a reagent is disposed on the first and second electrodes and no reagent on the third and fourth electrodes; the fifth electrode is disposed proximate the opening closest to one of the third and fourth electrodes; the reference electrode is disposed between the first and second electrodes; or the reference electrode extends to the opening of the passage closest to one of the third and fourth electrodes.

In the aforementioned aspects of the disclosure, the steps recited in the methods, such as, for example, determining, estimating, calculating, computing, deriving and/or utilizing (possibly in conjunction with an equation) may be performed be an electronic circuit or a processor. These steps may also be implemented as executable instructions stored on a computer readable medium; the instructions, when executed by a computer may perform the steps of any one of the aforementioned methods.

In additional aspects of the disclosure, there are computer readable media, each medium comprising executable instructions, which, when executed by a computer, perform the steps of any one of the aforementioned methods.

In additional aspects of the disclosure, there are devices, such as test meters or analyte testing devices, each device or meter comprising an electronic circuit or processor configured to perform the steps of any one of the aforementioned methods.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which:

FIG. 5B illustrates another logic diagram for determining error using the physical characteristic sensing electrodes and the working electrodes.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional. Also used herein, the phrase "electrical signal" or "signal" is intended to include direct current signal, alternating signal or any signal within the electromagnetic spectrum. The terms "processor"; "microprocessor"; or "microcontroller" are intended to have the same meaning and are intended to be used interchangeably. As used herein, the term "annunciated" and variations on its root term indicate that an announcement may be provided via text, audio, visual or a combination of all modes or mediums of communication to a user.

Figure 1:
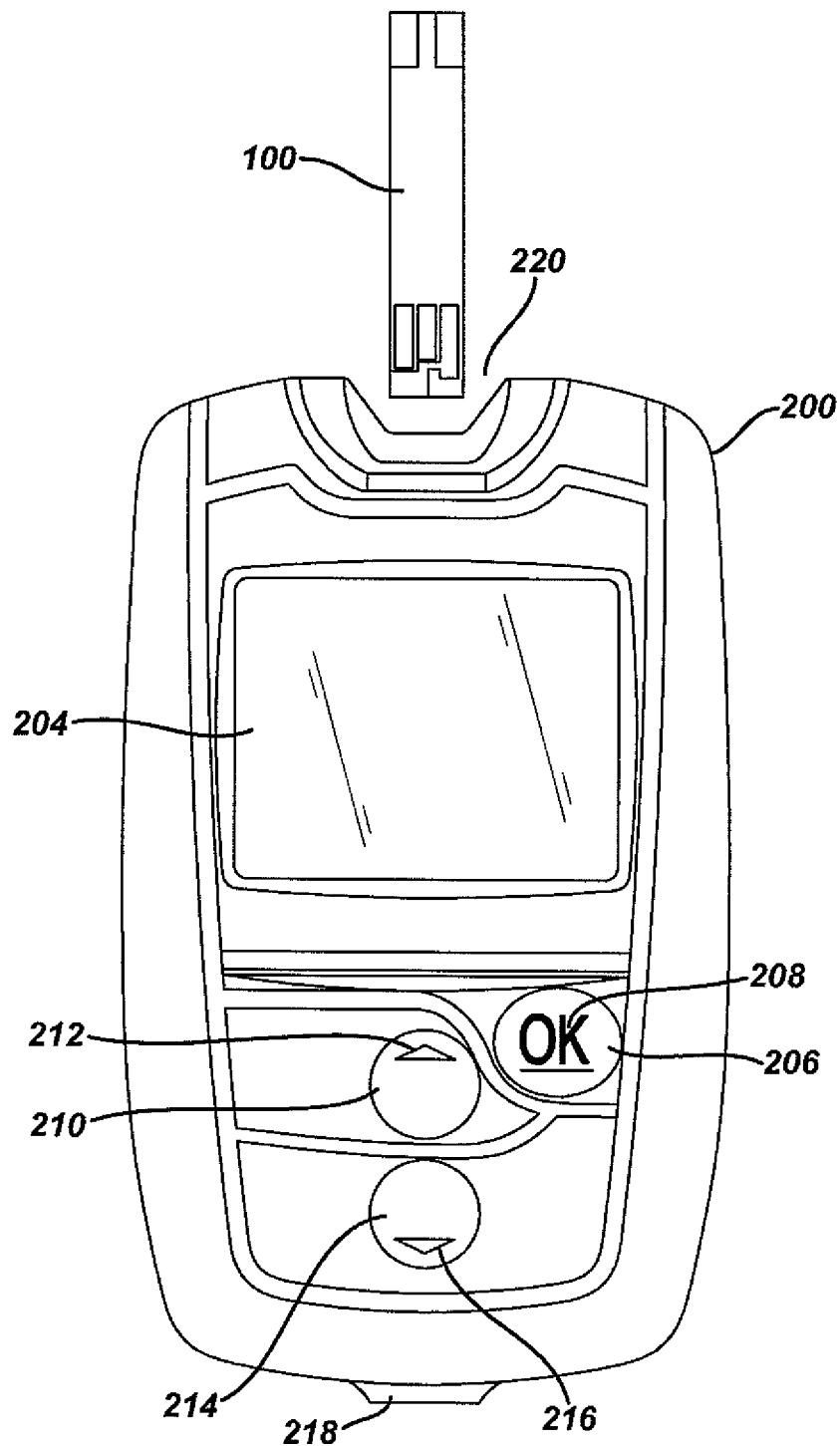
FIG. 1 illustrates an analyte measurement system.

FIG. 1 illustrates a test meter 200, for testing analyte (e.g., glucose) levels in the blood of an individual with a test strip produced by the methods and techniques illustrated and described herein. Test meter 200 may include user interface inputs (206, 210, 214), which can be in the form of buttons, for entry of data, navigation of menus, and execution of commands. Data can include values representative of analyte concentration, and/or information that are related to the everyday lifestyle of an individual. Information, which is related to the everyday lifestyle, can include food intake, medication use, the occurrence of health check-ups, general health condition and exercise levels of an individual. Test meter 200 can also include a display 204 that can be used to report measured glucose levels, and to facilitate entry of lifestyle related information.

Test meter 200 may include a first user interface input 206, a second user interface input 210, and a third user interface input 214. User interface inputs 206, 210, and 214 facilitate entry and analysis of data stored in the testing device, enabling a user to navigate through the user interface displayed on display 204. User interface inputs 206, 210, and 214 include a first marking 208, a second marking 212, and a third marking 216, which help in correlating user interface inputs to characters on display 204.

Test meter 200 can be turned on by inserting a test strip 100 (or its variants in the Priority Applications) into a strip port connector 220, by pressing and briefly holding first user interface input 206, or by the detection of data traffic across a data port 218. Test meter 200 can be switched off by removing test strip 100 (or its variants in the Priority Applications), pressing and briefly holding first user interface input 206, navigating to and selecting a meter off option from a main menu screen, or by not pressing any buttons for a predetermined time. Display 104 can optionally include a backlight.

In one embodiment, test meter 200 can be configured to not receive a calibration input for example, from any external source, when switching from a first test strip batch to a second test strip batch. Thus, in one exemplary embodiment, the meter is configured to not receive a calibration input from external sources, such as a user interface (such as inputs 206, 210, 214), an inserted test strip, a separate code key or a code strip, data port 218. Such a calibration input is not necessary when all of the test strip batches have a substantially uniform calibration characteristic. The calibration input can be a set of values ascribed to a particular test strip batch. For example, the calibration input can include a batch slope and a batch intercept value for a particular test strip batch. The calibrations input, such as batch slope and intercept values, may be preset within the meter as will be described below.

Figure 2A:
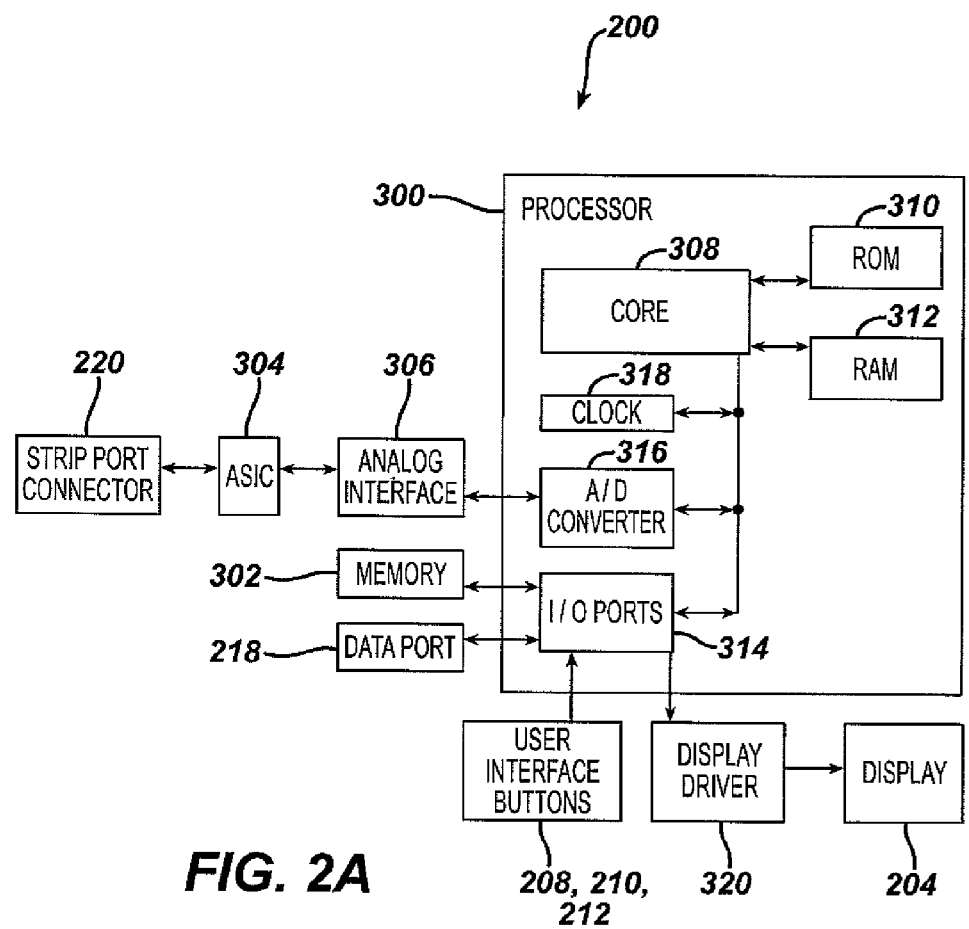
FIG. 2A illustrates in simplified schematic form the components of the meter 200.

Referring to FIG. 2A, an exemplary internal layout of test meter 200 is shown. Test meter 200 may include a processor 300, which in some embodiments described and illustrated herein is a 32-bit RISC microcontroller. In the preferred embodiments described and illustrated herein, processor 300 is preferably selected from the MSP 430 family of ultra-low power microcontrollers manufactured by Texas Instruments of Dallas, Tex. The processor can be bi-directionally connected via I/O ports 314 to a memory 302, which in some embodiments described and illustrated herein is an EEPROM. Also connected to processor 300 via I/O ports 214 are the data port 218, the user interface inputs 206, 210, and 214, and a display driver 320. Data port 218 can be connected to processor 300, thereby enabling transfer of data between memory 302 and an external device, such as a personal computer. User interface inputs 206, 210, and 214 are directly connected to processor 300. Processor 300 controls display 204 via display driver 320. Memory 302 may be pre-loaded with calibration information, such as batch slope and batch intercept values, during production of test meter 200. This pre-loaded calibration information can be accessed and used by processor 300 upon receiving a suitable signal (such as current) from the strip via strip port connector 220 so as to calculate a corresponding analyte level (such as blood glucose concentration) using the signal and the calibration information without receiving calibration input from any external source.

In embodiments described and illustrated herein, test meter 200 may include an Application Specific Integrated Circuit (ASIC) 304, so as to provide electronic circuitry used in measurements of glucose level in blood that has been applied to a test strip 100 (or its variants in the Priority Applications) inserted into strip port connector 220. Analog voltages can pass to and from ASIC 304 by way of an analog interface 306. Analog signals from analog interface 306 can be converted to digital signals by an A/D converter 316. Processor 300 further includes a core 308, a ROM 310 (containing computer code), a RAM 312, and a clock 318. In one embodiment, the processor 300 is configured (or programmed) to disable all of the user interface inputs except for a single input upon a display of an analyte value by the display unit such as, for example, during a time period after an analyte measurement. In an alternative embodiment, the processor 300 is configured (or programmed) to ignore any input from all of the user interface inputs except for a single input upon a display of an analyte value by the display unit. Detailed descriptions and illustrations of the meter 200 are shown and described in International Patent Application Publication No. WO2006040200, which is hereby incorporated by reference into this application as if fully set forth herein.

Figure 2B:
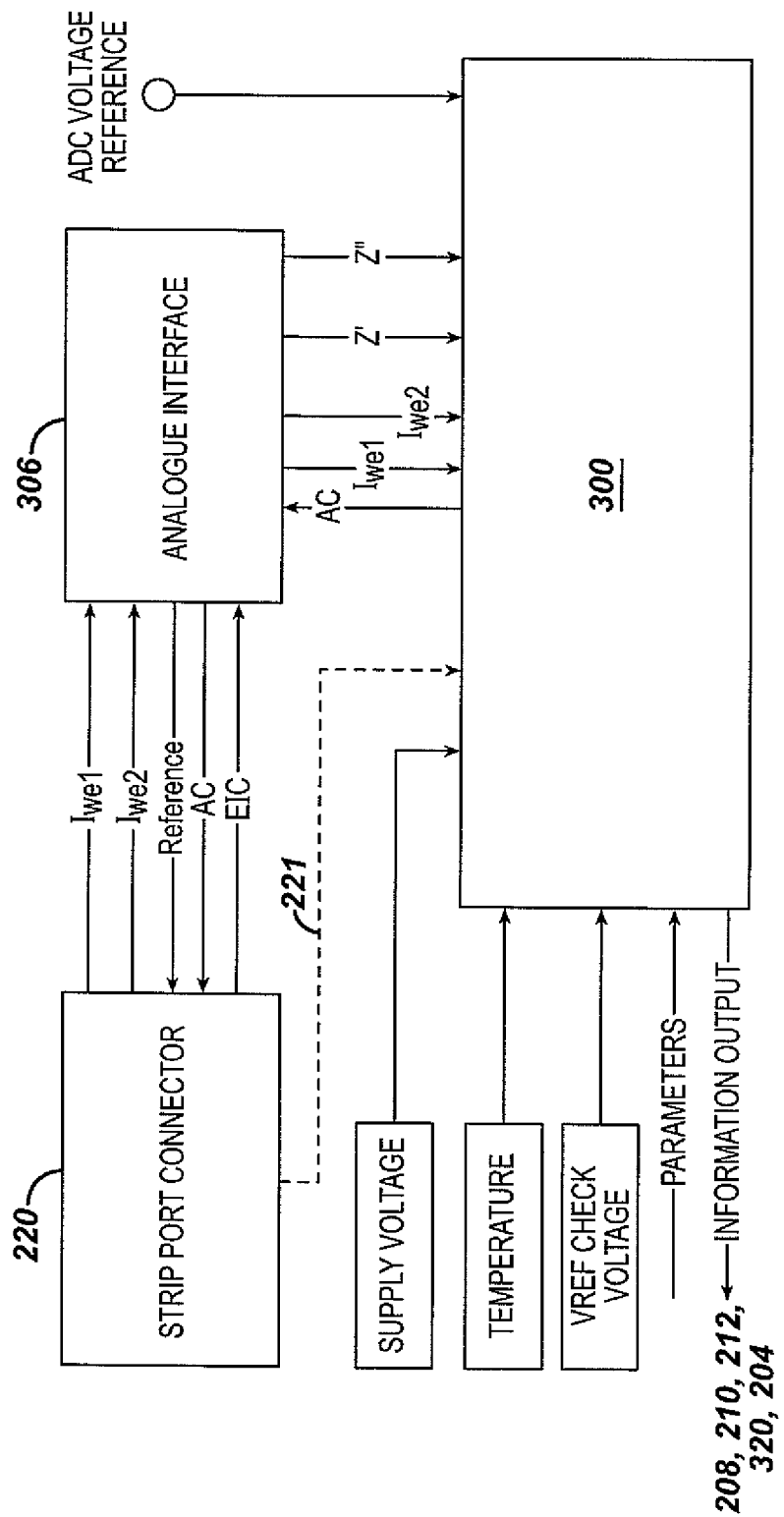
FIG. 2B illustrates in simplified schematic a preferred implementation of a variation of meter 200.
Figure 3A:
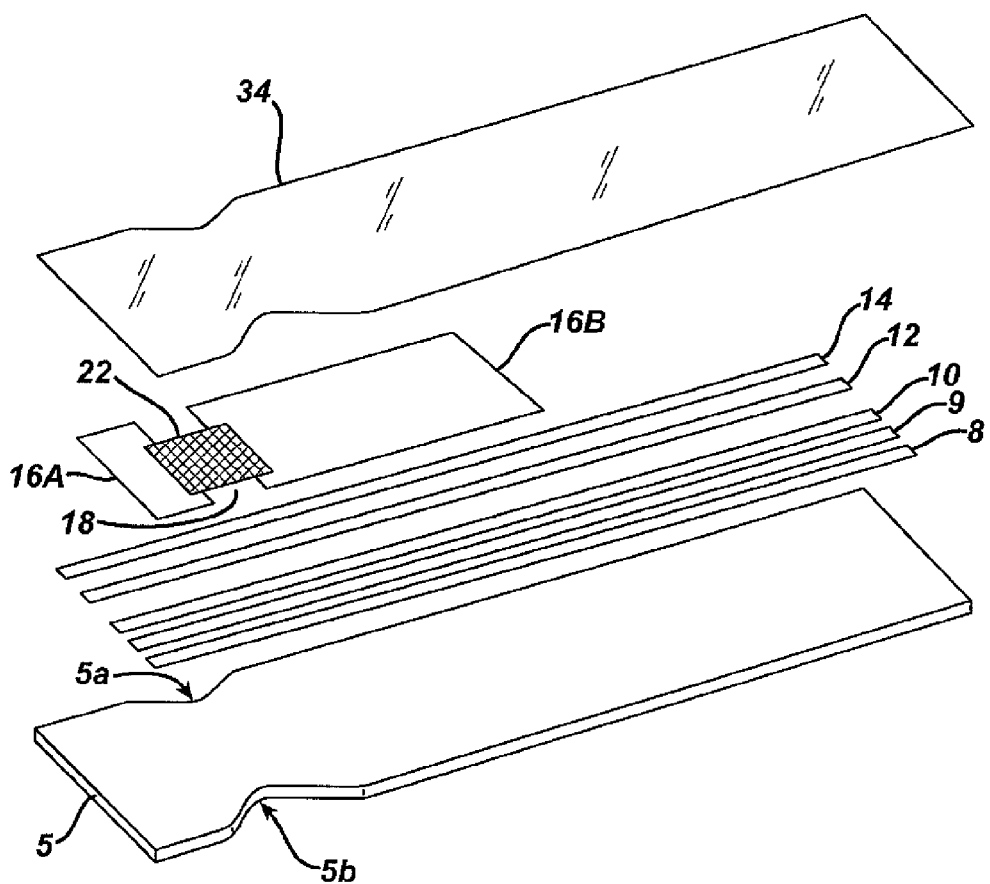
FIG. 3A illustrates an exploded view of one embodiment of the test strip 100 of the system of FIG. 1 in which there are two physical characteristic sensing electrodes and two analyte working electrodes.
Figure 3B:
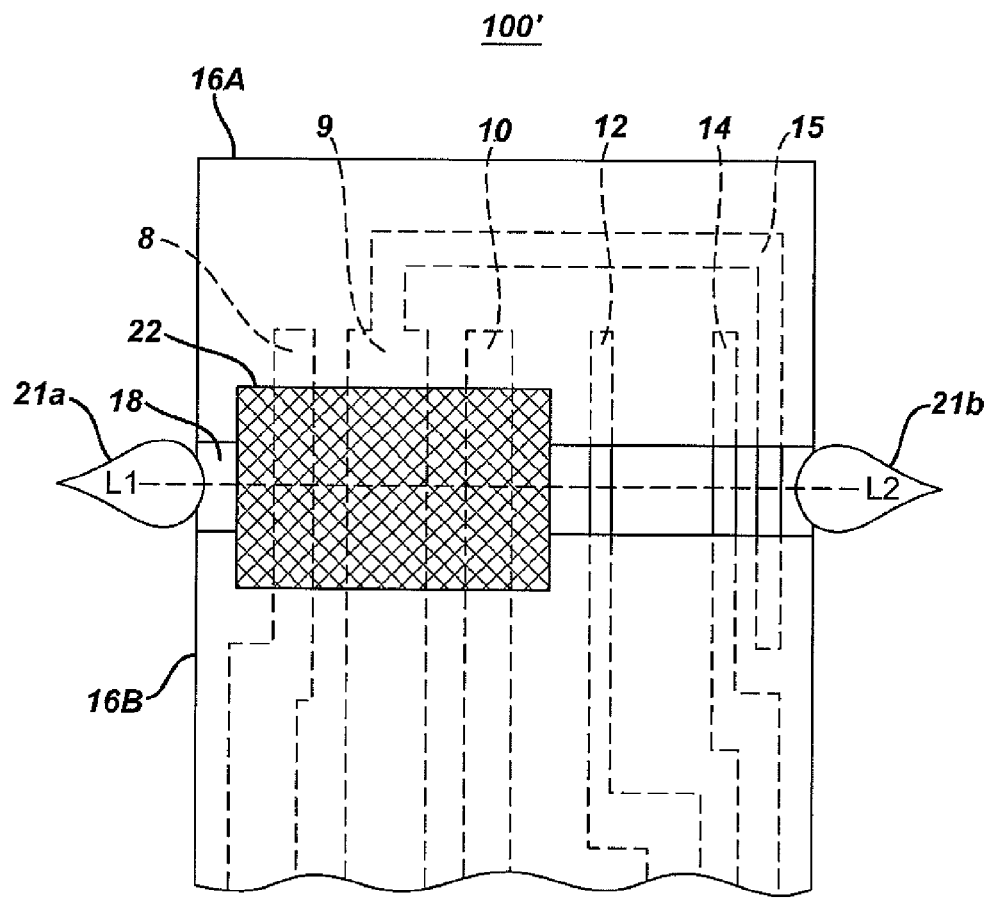
FIG. 3B illustrates a plan view of a variation of FIG. 3B.

Referring to FIG. 2B, details of a preferred implementation of meter 200 where the same numerals in FIGS. 2A and 2B have a common description. In FIG. 2B, a strip port connector 220 is connected to the analogue interface 306 by five lines including an impedance sensing line EIC to receive signals from physical characteristic sensing electrode(s), alternating signal line AC driving signals to the physical characteristic sensing electrode(s), reference line for a reference electrode, and current sensing lines from respective working electrode 8 and working electrode 10 (FIGS. 3A and 3B). A strip detection line 221 can also be provided for the connector 220 to indicate insertion of a test strip. The analog interface 306 provides four inputs to the processor 300: (1) real impedance Z'; (2) imaginary impedance Z"; (3) output signal sampled or measured from working electrode 8 of the biosensor or $I_{we1}$; (4) output signal sampled or measured from working electrode 10 of the biosensor or $I_{we1}$. There is one output from the processor 300 to the interface 306 to drive an oscillating signal AC of any value from 25 kHz to about 250 kHz or higher to the physical characteristic sensing electrodes 12 and 14 (FIGS. 3A and 3B). A phase differential P (in degrees) or modulus of impedance Z (in ohms) can be determined from the real impedance Z' and imaginary impedance Z" as shown and described in prior filed international patent applications PCT/GB2012/053276, PCT/GB2012/053277 PCT/GB2012/053279 (all filed on Dec. 28, 2012), which are incorporated by reference into this application as if set forth herein.

FIG. 3A illustrates a multi-layer test strip 100 starting with a substrate 5 on which a first conductive layer may include first electrode 8, counter or reference electrode 9, second electrode 10, third electrode 10, fourth electrode 12, and fifth electrode 14. A second layer may include non-conductive portions 16A and 16B with a reagent 22 disposed in a flow passage 18. A final layer can be provided with cover 34. It should be noted that additional layers can be provided, as shown and described in PCT/GB2012/053276, which is incorporated by reference herein to this application.

As shown in FIG. 3B, a variation 100' of the strip 100 (FIG. 3B) is shown in which the counter or reference electrode 9 can be utilized with a fifth electrode 15 for use with the third and fourth physical characteristic sensing electrodes 12 and 14. The physical characteristic sensing electrodes 12 and 14 are provided with respective electrode tracks. The fifth electrode 15 can be provided to act as grounding or shielding electrode due to the capacitive effect of the alternating signals being applied to the third and fourth electrodes. The fifth electrode 15 is used to reduce or eliminate any capacitance coupling between the finger or body of the user and the characteristic measurement electrodes 12 and 14. The grounding electrode 15 allows for any capacitance due to coupling with a user's anatomy to be directed away from the sensing electrodes 12 and 14. To do this, the grounding electrode 15 can be connected to any one of the other five electrodes or to its own separate contact pad (and track) for connection to ground on the meter instead of one or more of contact pads on the test strip. In a preferred embodiment, the grounding electrode 15 is connected to one of the three electrodes that has reagent 22 disposed thereon. In a most preferred embodiment, the grounding electrode 15 is connected to reference electrode 9.

Referring back to FIG. 3A, a reagent layer 22 can be deposited on the electrodes 8, 9, and 10 and a non-conductive layer defined by cover 16A and 16B can be disposed on the first layer and the reagent. Alternatively, the reagent 22 can be deposited on the electrodes and the passage defined by the separation between the covers 16A and 16B. The covers 16A and 16B are disposed such that they define a passage 18 along axis L1-L2 through which first and second openings 5A and 5B are provided on the side edge of the substrate 5.

In all of these embodiments, the physical characteristic sensing electrodes 12 and 14 are spaced apart from the reagent layer 22 so that these sensing electrodes are virtually or actually unaffected by the electrochemical reaction of the reagent in the presence of a fluid sample (e.g., blood or interstitial fluid) containing the requisite analyte such as glucose.

As is known, conventional electrochemical-based analyte test strips employ a working electrode along with an associated counter/reference electrode and enzymatic reagent layer to facilitate an electrochemical reaction with an analyte of interest and, thereby, determine the presence and/or concentration of that analyte. For example, an electrochemical-based analyte test strip for the determination of glucose concentration in a fluid sample can employ an enzymatic reagent that includes the enzyme glucose oxidase and the mediator ferricyanide (which is reduced to the mediator ferrocyanide during the electrochemical reaction). Such conventional analyte test strips and enzymatic reagent layers are described in, for example, U.S. Pat. Nos. 5,708,247; 5,951,836; 6,241,862; and 6,284,125; each of which is hereby incorporated by reference herein to this application. In this regard, the reagent layer employed in various embodiments provided herein can include any suitable sample-soluble enzymatic reagents, with the selection of enzymatic reagents being dependent on the analyte to be determined and the bodily fluid sample. For example, if glucose is to be determined in a fluid sample, enzymatic reagent layer 22 can include glucose oxidase or glucose dehydrogenase along with other components necessary for functional operation.

In general, enzymatic reagent layer 22 includes at least an enzyme and a mediator. Examples of suitable mediators include, for example, ruthenium, Hexaammine Ruthenium (III) Chloride, ferricyanide, ferrocene, ferrocene derivatives, osmium bipyridyl complexes, and quinone derivatives. Examples of suitable enzymes include glucose oxidase, glucose dehydrogenase (GDH) using a pyrroloquinoline quinone (PQQ) co-factor, GDH using a nicotinamide adenine dinucleotide (NAD) co-factor, and GDH using a flavin adenine dinucleotide (FAD) co-factor. Enzymatic reagent layer 22 can be applied during manufacturing using any suitable technique including, for example, screen printing.

Applicants note that enzymatic reagent layer may also contain suitable buffers (such as, for example, Tris HCl, Citraconate, Citrate and Phosphate), hydroxyethylcelulose [HEC], carboxymethylcellulose, ethycellulose and alginate, enzyme stabilizers and other additives as are known in the field.

Further details regarding the use of electrodes and enzymatic reagent layers for the determination of the concentrations of analytes in a bodily fluid sample, albeit in the absence of the phase-shift measurement electrodes, analytical test strips and related methods described herein, are in U.S. Pat. No. 6,733,655, which is hereby fully incorporated by reference herein to this application.

In the various embodiments of the test strip, there are two measurements that are made to a fluid sample deposited on the test strip. One measurement is that of the concentration of the analyte (e.g. glucose) in the fluid sample while the other is that of physical characteristic (e.g., hematocrit) in the same sample. The measurement of the physical characteristic (e.g., hematocrit) is used to modify or correct the glucose measurement so as to remove or reduce the effect of red blood cells on the glucose measurements. Both measurements (glucose and hematocrit) can be performed in sequence, simultaneously or overlapping in duration. For example, the glucose measurement can be performed first then the physical characteristic (e.g., hematocrit); the physical characteristic (e.g., hematocrit) measurement first then the glucose measurement; both measurements at the same time; or a duration of one measurement may overlap a duration of the other measurement. The measurement for the physical characteristic (among other measurements) is shown and described in prior filed applications PCT/GB2012/053276, PCT/GB2012/053277 PCT/GB2012/053279 (all filed on Dec. 28, 2012), which are incorporated by reference into this application as if fully set forth herein. The measurement for glucose is discussed in detail as follow with respect to FIGS. 4A and 4B. Additional details of the measurement for glucose in conjunction with the sensed physical characteristic(s) are also shown and described in PCT/GB2012/053276, PCT/GB2012/053277 PCT/GB2012/053279, which are incorporated by reference into this application as if fully set forth herein. A copy of PCT/GB2012/053276 noted in this paragraph is also attached herewith in the Appendix.

Figure 4A:
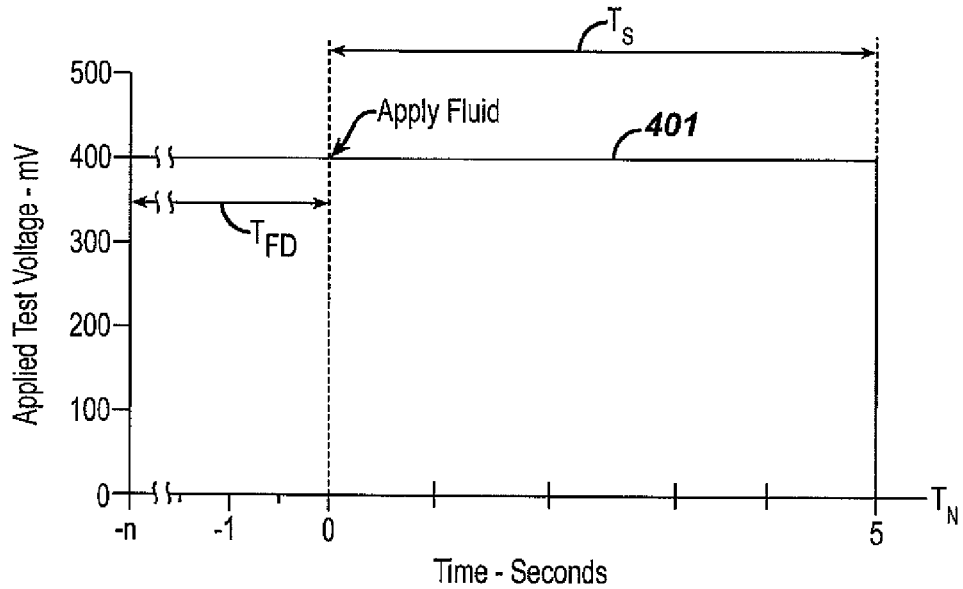
FIGS. 4A and 4B illustrate time to signal graphs applied to the test strip and signal measured or sampled from the test strip.

FIG. 4A is an exemplary chart of a test signal applied to test strip 100. Before a fluid sample is applied to test strip 100 (or its variants in the Priority Applications), test meter 200 is in a fluid detection mode in which a first test signal of about 400 millivolts is applied between second working electrode and reference electrode. A second test signal 401 of about 400 millivolts is preferably applied simultaneously between first working electrode (e.g., electrode 8 of strip 100) and reference electrode (e.g., electrode 9 of strip 100). Alternatively, the second test signal may also be applied contemporaneously such that a time interval of the application of the first test signal overlaps with a time interval in the application of the second test voltage. The test meter may be in a fluid detection mode during fluid detection time interval $T_{FD}$ prior to the detection of physiological fluid at starting time at zero. In the fluid detection mode, test meter 200 determines when a fluid is applied to test strip 100 (or its variants in the Priority Applications) such that the fluid wets either first working electrode 8 or second working electrode 10 and reference electrode 9. Once test meter 200 recognizes that the physiological fluid has been applied because of, for example, a sufficient increase in the measured test current at either the first working electrode 8 or second working electrode 10 (or both electrodes) with respect to the reference electrode 9, test meter 200 assigns a zero second marker at zero time "0" and starts the test sequence time interval $T_S$. Test meter 200 may sample the current transient output at a suitable sampling rate, such as, for example, every 1 milliseconds to every 100 milliseconds. Upon the completion of the test time interval $T_S$, the test signal is removed. For simplicity, FIG. 4A only shows the first test signal 401 applied to test strip 100 (or its variants in the Priority Applications).

Figure 4B:
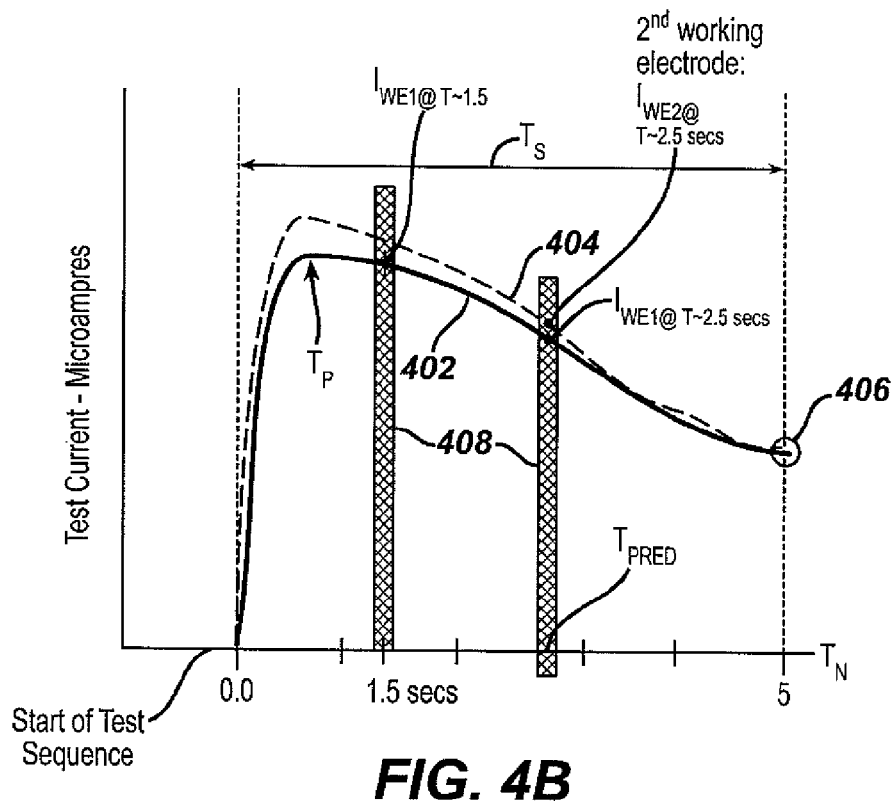

In FIG. 4A, the first and second test voltages applied to test strip 100 (or its variants in the Priority Applications) are generally from about +100 millivolts to about +600 millivolts. In one embodiment in which the electrodes include carbon ink and the mediator includes ferricyanide, the test signal is about +400 millivolts. Other mediator and electrode material combinations will require different test voltages, as is known to those skilled in the art. The duration of the test voltages is generally from about 1 to about 5 seconds after a reaction period and is typically about 3 seconds after a reaction period. Typically, test sequence time $T_S$ is measured relative to zero set time $t_0$. As the voltage 401 is maintained in FIG. 4A for the duration of $T_S$, output signals are generated, shown here in FIG. 4B with the current transient 402 for the first working electrode 8 being generated starting at zero time and likewise the current transient 404 for the second working electrode 10 is also generated with respect to the zero time. It is noted that while the signal transients 402 and 404 have been placed on the same referential zero point for purposes of explaining the process, in physical term, there is a slight time differential between the two signals due to fluid flow in the chamber towards each of the working electrodes 8 and 10 along axis L1-L2. However, the current transients are sampled and configured in the microcontroller to have the same start time. In FIG. 4B, the current transients build up to a peak proximate peak time Tp at which time, the current slowly drops off until approximately one of 2.5 seconds or 5 seconds after zero time. At point 406, approximately at 5 seconds, the output signal for each of the working electrodes 8 and 10 may be measured and added together. Alternatively, the signal from only one of the working electrodes 8 and 10 can be doubled. From knowledge of the parameters of the test strip (e.g., batch calibration code offset and batch slope) for the particular test strip 100 and its variations, the analyte (e.g., glucose) concentration can be calculated. Output transient 402 and 404 can be sampled to derive signals $I_E$ (by summation of each of the current $I_{WE1}$ and $I_{WE2}$ or doubling of one of $I_{WE1}$ or $I_{WE2}$) at various time positions during the test sequence.

It is worthwhile here to note that even before the system can measure the output signals reflective of the analyte concentration, the system must be able to determine whether the test strip has been adequately filled. Put another way, the system must be able to determine whether the relevant electrodes have been covered with enough sample such that an analyte measurement test can be conducted. One challenge with the particular strip configurations provided herein is that the test strip can be filled on either side of the test strip at entrance 5A or 5B. Because the strip is intended to be filled from only one side, a fill from both sides of the strip would constitute an error. Additionally, the system needs to know which side is being filled to initiate the appropriate algorithms (analyte measurement first before impedance measurement or impedance measurement before analyte measurement). To solve these challenges, we have devised these techniques described herein to determine whether the test strip has been filled correctly or an error has been made in the filling of the test strip.

Specifically, in the first technique, we have devised a monitoring of the working electrodes such that it is possible to determine fill direction/location by determining which electrode breaches a predetermined threshold first. This applies to systems with a plurality of electrodes in a number of orientations (in addition to the ones shown in FIGS. 3A and 3B). Further, in the second technique, for systems which have analyte measurements along with physical characteristic measurement, it is also possible to achieve the same objectives by determining when each measurement (analyte measurement versus physical characteristic measurement) happens relative to the other. For test strip which can be filled from either side, the role of any electrode can change depending on the determination of fill direction. For example a measurement electrode can double up as a fill detect/full sufficiency electrode if it is determined that based on fill direction this electrode is now the last electrode in the chamber.

Figure 5A:
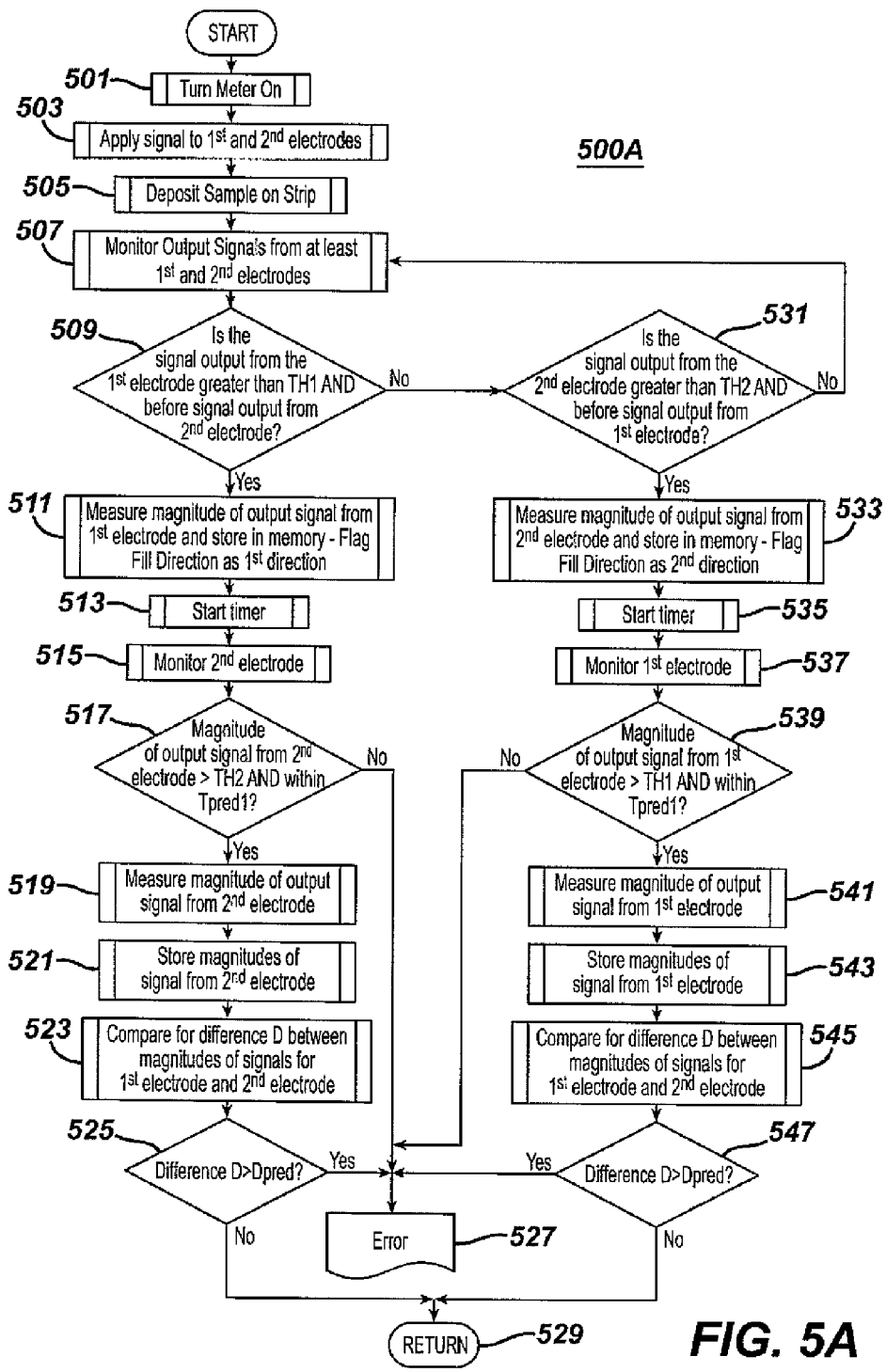
FIG. 5A illustrates a logic diagram for determining error during a fill sequence using the working electrodes for the test strip of FIGS. 3A and 3B.

As such, one of the implementations of the disclosure can be understood with reference to FIG. 5A. In FIG. 5A, logical process 500A is provided to determine fill error for a test strip having at least two electrodes disposed in a passage extending between first and second openings 5A and 5B. The process can be initiated with step 501 by activation of the meter. At step 503, the system applies a signal (e.g., 400 mV in FIG. 4A) to first and second electrodes 8 and 10. At step 505, it is assumed that a sample would be deposited into one of the first and second openings 5A and 5B. At step 507, the output signals from the first electrode 8 or second electrode 10 are monitored for a significant increase or rate of increase (FIG. 4B) in current which is reflective of an electrochemical reaction. At step 509, a query is made as to whether the first electrode 8 outputs a signal greater than a first threshold TH1 before the second electrode and if true, the logic moves to step 511. On the other hand, if the query 509 returns a false then another query is made at step 531 to determine if the output signal is at the second electrode 10 is greater than a second threshold TH2 before a signal output from the first electrode 8 is greater than the first threshold TH1. If true at step 531, the logic moves to step 533 otherwise the logic returns to the monitoring step 507.

Returning to step 509, it is assumed that query 509 returns a true and therefore it is assumed that the test strip has been filled from the left at opening 5A and steps 511-527 may be undertaken. In particular, at step 511, a time zero point of the test sequence $T_S$ can be designated and the signal output 402 can be measured from T=0.0 to $T_N$ for the analyte concentration. At step 513, a timer T can be started, among other tasks, for measurements of the output signal from the first electrode 8. At step 515, the second electrode 10 is monitored or measured for a signal output within a predetermined time period (to return a yes in step 515) or else reporting a fill error when the signal output of the other electrode is after the predetermined time period (returning a no in step 515). In the case where query 515 returns a false (i.e., the sample has not reached the second electrode within a predetermine time $T_{pred1}$) then the system annunciates an error at step 527 indicative of the inability of the sample to sufficiently fill the passage 18. It is noted here that the predetermined time $T_{pred1}$ is the time for a sample to flow from first electrode 8 to electrode 10 or vice versa. On the other hand, where the sample has flowed from the first electrode 8 past reference electrode 9 to second electrode 10 in a sufficient amount to output a signal greater than a second threshold TH2 at step 517 within the predetermined time $T_{pred1}$, the query at step 517 returns a yes whereby another timer sets a starting time for sampling the magnitudes of the output signal 404 from the second electrode through the test sequence from T=0.0 to $T_N$ can be measured or sampled. On the other hand, if the sample is deposited in the second opening, the second electrode would output a signal greater than a second threshold TH2 before the output signal from the first electrode 8. Thus, the query 531 would return a true condition, leading to step 537 where it is determined whether sufficient sample has crossed from the second electrode to the first electrode (sample 21b moving right to left in FIG. 3B) within a predetermined time period $T_{pred1}$. If these conditions are not met, an error is provided at step 527. If these conditions are met then the logic proceeds towards an analyte measurements. To restate steps 509, 515, 517, 527 and steps 531, 533, 539, 527: in the event the first electrode 8 or the second electrode 10 outputs a signal before the other of the first and second electrodes then monitoring the other of the first and second electrodes for a signal output within a predetermined time period $T_{pred1}$ otherwise the system will report a fill error when the signal output is after the predetermined time period $T_{pred1}$.

While queries 509, 517 and 531 and 539 are designed to detect the whether the sample has flowed from first electrode 8 to the second electrode 10 (i.e., sample 21a moving left to right in FIG. 3B) or from the second electrode 10 to the first electrode 8 (sample 21b moving right to left in FIG. 3B) by virtue of queries 531 and 539, these queries cannot determine if a sufficient sample (i.e., a sample sufficient to conduct an analyte measurement test within its intended use and specification) has been provided. In both of these scenarios, in order to determine if a sufficient sample has been provided, the system would measure or sample the signal outputs 402 and 404 (FIG. 4B) from the respective first and second electrodes 8 and 10 at step 511 and 519 (or at steps 533 and 541). A value representative of one of the outputs 402 and 404 are compared with the representative of the other output at step 523 (or step 545). Where a difference between the two signal outputs 402 and 404 (which can be a single point in time for each transient or a summation of the transient over a selected duration) is greater than a predetermined difference $D_{pred}$ at step 523 (or step 545), it can be inferred that there has been insufficient volume of the sample deposited on the strip and an error can be annunciated at step 527 or flagged for later utilization.

In particular, where the sample 21a is moving from left to right in FIG. 3B as determined by steps 511 and 517, the system measures the output signal from the second electrode 10 during the test sequence $T_S$ at step 519. At step 523, the system compares at a magnitude of the signal from the second electrode with magnitude of the signal from the first electrode 8 during a sampling interval $T_{PRED}$ within the test sequence $T_S$ (FIG. 4B). At step 525, the difference between the two measurements is compared with a predetermined threshold $D_{pred}$. At step 527, the system reports an error if the magnitude of the signal from the second electrode 10 is different from the magnitude of the signal from the first electrode 8 during a sampling interval $T_{PRED}$ within the test sequence $T_S$ greater than the predetermined threshold. However, if the difference is within a predetermined amount (e.g., 10-30%), the system adds the magnitudes of the signals and calculate an analyte concentration based on the summed magnitudes. The calculation of the analyte concentration is shown and described in PCT/GB2012/053276, PCT/GB2012/053277 PCT/GB2012/053279 (all filed on Dec. 28, 2012), which are incorporated by reference into this application as if fully set forth herein.

On the other hand, where the sample (21b) is moving from right to left in FIG. 3B as determined by steps 533 and 539, the system further measures the magnitude of the output signal of the first electrode at step 541 during a sampling interval $T_{PRED}$ within the test sequence $T_S$. Thereafter, the system compares at step 545 the magnitude of the respective output signals from the first electrode 8 and the second electrode 10 during a sampling interval $T_{PRED}$ within the test sequence $T_S$. At step 547, the difference between the two analyte measurements (one from each electrode 8 and 10) is determined with respect to the predetermined differential threshold $D_{pred}$. At step 527, the system reports an error if the magnitude of the signal from the second electrode 10 is different by a predetermined differential (e.g., in percent) from the magnitude of the signal from the first electrode 8 during a sampling interval $T_{PRED}$ within the test sequence $T_S$. However, if the differential is within a predetermined amount (e.g., 10-30%), the system adds the magnitudes of the signals and calculate an analyte concentration based on the summed magnitudes. It is noted that while we have shown the sampling time interval $T_{PRED}$ as a small subset of the test sequence $T_S$, the sampling interval $T_{PRED}$ can be of the same magnitude as the test sequence $T_S$.

Where the test strip has additional electrodes to sense or detect a physical characteristic of the sample, such as, for example, hematocrit, density, or temperature, such additional electrodes can also be utilized in the fill detection technique devised by us.

In particular, we have devised another technique to take advantage of the additional sensing electrodes 12 and 14 (FIGS. 3A and 3B) as illustrated in the logical process 500B of FIG. 5B. In this technique, the process 500B begins with the activation of the meter at step 502 at which point the system will apply input signals to the first electrode 8, second electrode 10, third electrode 12, and fourth electrode 14. Upon deposition of the sample into one of the openings 5A or 5B, the system immediately monitor the electrodes for output signals from at least the electrodes 8, 10, 12, and 14 at step 508. At step 510 a query is made to determine if the sample has been applied at first opening 5A by determining if the first electrode is outputting a signal with a magnitude greater than a first threshold TH1 before any output signal from the third or fourth electrodes 12 or 14 that has a magnitude greater than a third threshold TH3. If the query at step 510 returns a no, meaning that the sample has not been applied in opening 5A, the system performs another query at step 514 to determine if a sample has been applied in the other opening 5B be determining whether a signal output from the third and fourth electrodes 12 and 14 is greater than the third threshold TH3 and before any signal output from the first or second electrodes 8 or 10. If the query at step 514 returns a no, meaning that a sample has not been applied at the second opening 5B, the system performs a third query to determine if the output signal from the second electrode 10 is greater than the second threshold TH2 before any signal from the first, third, or fourth electrodes 10, 12, or 14. If the query at step 516 returns a yes, this means that there is an inconsistency between the query 514 and query 516 and therefore an error condition must exist where a second electrode 10 has detected a sample but none of the first, third and fourth electrodes 8, 12, or 14 has detected such a sample. Hence, at step 558, an error is annunciated to the user or flagged for later utilization in the main routine.

Returning back to the query 510, if the query 510 indicates that a sample has been detected by the first electrode, implying that the strip has been filled from the first opening 5A (sample 21a moving from left to right in FIG. 3B), the process moves to step 518 whereby a test sequence timer is set to 0 and the current transient output of the first electrode 8 is measured for a predetermined interval $T_{PRED}$ during the test sequence time $T_S$. At step 520, a timer can be started for measuring, among other intervals, a predetermined interval Tpred1 expected for a sample to cross from the first electrode 8 to the second electrode 10. At step 522, the second electrode 10 is monitored for a rise in output signal. A query is made at step 524 to determine if such is the case. If true, the logic moves to step 526 whereby a timer is set to zero to start the test sequence time $T_S$ and the second electrode 10 is sampled during a predetermined sampling interval $T_{PRED}$ in the test sequence time $T_S$. The magnitude of the output signals during the predetermined sampling time interval is stored at step 528. At this point, the additional physical characteristic sensing electrodes 12 and 14 can be used to infer that both of the first and second electrodes 8 and 10 have been filled with an adequate sample volume. The system does this at step 530 by checking to see if signal outputs from the third and fourth electrodes 12 and 14 have exceeded the third threshold TH3 with in a second predetermined time $T_{pred2}$. If true at step 530, the logic can (a) move directly to the main routine to complete the analyte assaying at step 560 or (b) conduct another fill sufficiency test by comparing the difference in analyte level as measured by the first electrode 8 and the analyte level as measured by the second electrode 10 in step 532 and if the difference between the two measured analyte concentrations are greater than a predetermined value, an error is annunciated at step 536 or flagged for post measurement error handling. In the post-measurement error handling, the error flagged at step 536 (or step 558) can be used in the determination of the main subroutine to decide whether to abort the analyte assay measurement or continue on with the assay but instead of displaying the analyte measurement at the end of the assay, an error message would be provided.

Returning back to the query 514, if the query 514 indicates that a sample has been detected by the third and fourth electrodes 12 and 14 at a magnitude greater than TH3 and before the signal output from either of the first or second electrode 8 or 10, implying that the strip has been filled from the second opening 5B (i.e., the sample 21b moving from right to left in FIG. 3B), the process moves to step 538. Since there is an inference that the fluid sample will arrive at the second electrode 10 first, the system monitors the first electrode at step 538 and the second electrode at step 540 for a significant rise in output signals from these electrodes above the respective first and second thresholds TH1 and TH2. At step 542, if the output signal from the first electrode 8 is greater than the first threshold and before a significant output signal from the second electrode 10, this implies that a sample might have also been additionally applied to the first opening 5A concurrently with the second opening 5B. Hence at step 542, the query would be a true statement resulting in an error being annunciated or flagged at step 536. If query 542 is false then the logic moves to step query 544 where the magnitude of the second electrode 10 is measured to determine if it is greater than the second threshold TH2 and before a significant output signal from the first electrode 8. If query 544 is true then the system moves to the next step 546 otherwise if the query is false, an error is annunciated or flagged at step 536. At step 546, the logic initiates a timer at time zero for the test sequence $T_S$ and starts the timer for sampling the magnitudes of signal output such that the measured magnitudes of the second electrode 10 can be used to calculate the analyte concentration. At step 548, a query is made as to whether the magnitude of the output signal from the first electrode 8 is greater than the first threshold TH1 and within a first predetermined time $T_{pred1}$ (i.e., the time it takes for the sample to move from the second electrode 10 to the first electrode 8 and vice versa). If the query at step 548 is false, an error is annunciated or flagged at step 536. If true at query 548, the logic moves to measure the magnitude of the first electrode at step 550. The resulting magnitudes of the first electrode 8 during the test sequence $T_S$ at step 550 are stored at step 552 for comparison with the stored resulting magnitudes during the test sequence $T_S$ for the second electrode 10. At step 552, the logic can (a) move directly to the main routine to complete the analyte assaying at step 560 or (b) conduct another fill sufficiency test by comparing the difference in analyte level as measured by the first electrode 8 and the analyte level as measured by the second electrode 10 in step 554 and if the difference between the two measured analyte concentrations are greater than a predetermined value, an error is annunciated at step 536 or flagged for post measurement error handling.

Figure 5C:
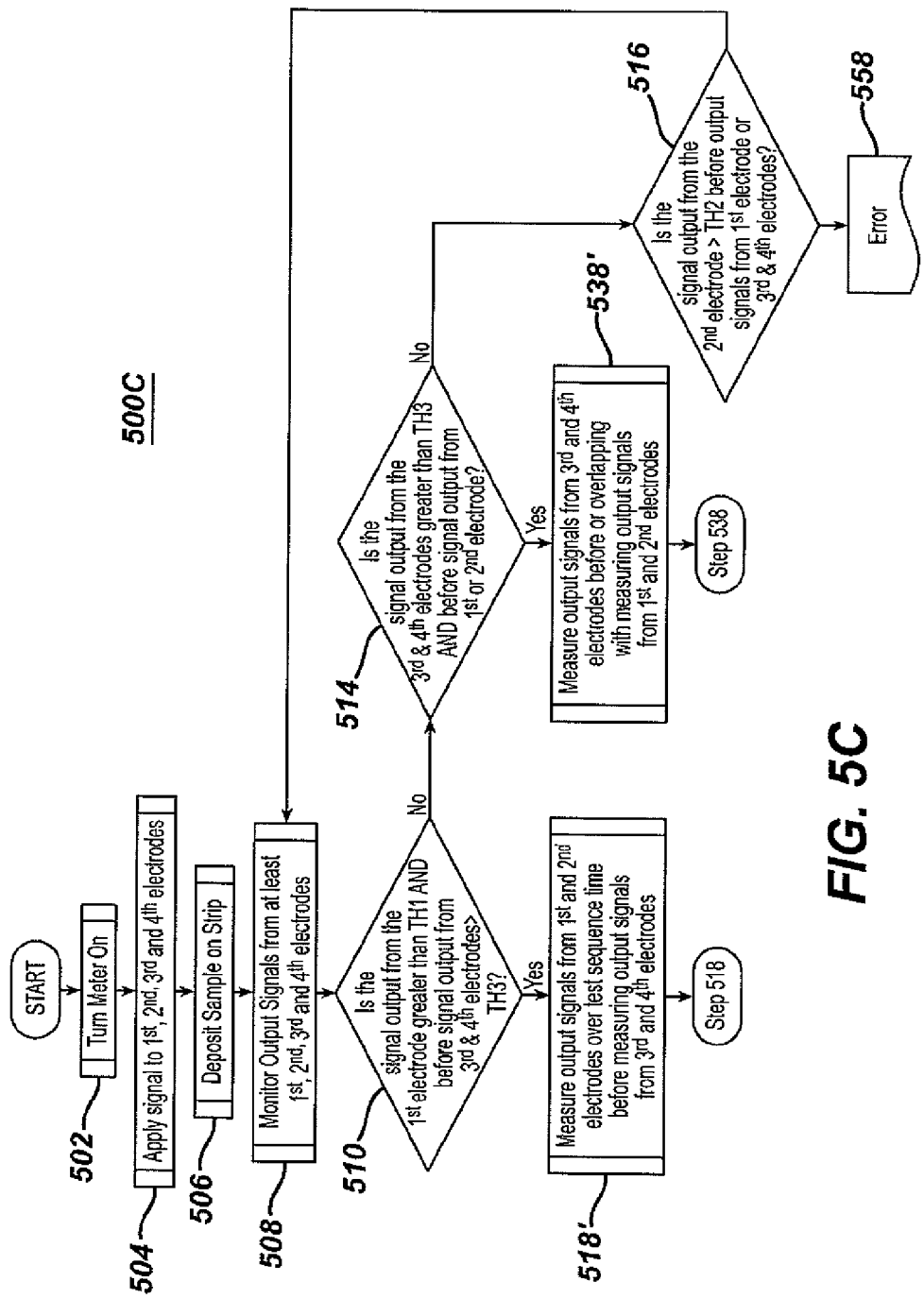
FIG. 5C illustrates a variation on the logic diagram of FIG. 5B to show the steps for selecting different measurement techniques depending on the direction of sample filling the test strip.

We have also devised a technique to determine one of the directions that a sample has taken upon deposition of the sample into one of the openings 5A and 5B. This technique is embedded within the technique illustrated in FIG. 5B. For brevity, only the relevant steps are shown in FIG. 5C but it should be clear that the explanation for the same reference numbers in FIG. 5B would apply in FIG. 5C. In FIG. 5C, the method can be achieved by activation of the meter at step 502 to apply signals to the first through fourth electrodes in step 504, deposition of the sample into one of the openings 5A or 5B at step 506. Upon deposition of the sample, which can be detected by one of the electrodes as an increase in output signal, the system immediately monitor the electrodes for output signals from at least the electrodes 8, 10, 12, and 14 at step 508. As in FIG. 3B, at step 510 a query is made to determine if the sample has been applied at first opening 5A by determining if the first electrode is outputting a signal with a magnitude greater than a first threshold TH1 before any output signal from the third or fourth electrodes 12 or 14 that has a magnitude greater than a third threshold TH3. If the query 510 indicates that a sample has been detected by the first electrode 8, implying that the strip has been filled from the first opening 5A (sample 21a moving from left to right in FIG. 3B), the process moves to step 518' which selects a first measurement based on output signals from each of the first and second electrodes before a second measurement based on output signals from the third and fourth electrodes during the test sequence. In other words, step 518' would configure the system to collect output signals from the first and second electrodes during test sequence time TS before the collection of the output signals from the third and fourth electrodes. Alternatively, the collection of the signals from the third and fourth electrodes would be after the start of the collection of the signals from the first and second electrodes resulting in an overlap of the two measurement collections. As in FIG. 5B, the logic in this flow chart would revert to the remaining steps in FIG. 5B, starting with step 518.

On the other hand, at step 514, if the third and fourth electrodes output a signal greater than a third threshold (TH3) and before any output signal from one of the first and second electrodes 8 and 10 then the logic selects, at step 538', the second measurement based on output signals from the third and fourth electrodes before the first measurement based on output signals from each of the first and second electrodes. In other words, step 538' would configure the system to collect output signals from the third and fourth electrodes 12 and 14 during before the collection of the output signals from the first and second electrodes 8 and 10. Alternatively, the collection of the signals from the first and second electrodes 8 and 10 would be after the start of the collection of the signals from the third and fourth electrodes 12 and 14 resulting in an overlap of the two measurement collections. As in FIG. 5B, the logic in this flow chart would revert to the remaining steps in FIG. 5B, starting with step 538.

In the embodiments described herein, the first threshold TH1 is about 150 nanoamps or 0.15 microamps; the second threshold TH2 is about 0.15 microamps; the third threshold TH3 is about 100 nanoamps or 0.1 microamps. Alternatively, if AC signals are utilized to monitor the movement of the fluid sample from the first or the second openings, the thresholds would be in magnitude of impedance such as, for example, 10 kilo-Ohms to 100 kilo-Ohms Likewise, the threshold (by itself or with the impedance threshold) can be from about 90 degrees to less than 45 degrees in phase angles. Where different materials are utilized in the test strip, the thresholds may change. However, the principles of the invention would still apply and once apprised by the disclosure herein, one skilled in the art would be able to derive the required thresholds; the predetermined sampling time $T_{PRED}$ is about 100 milliseconds at any time point during the test sequence time $T_S$; the test sequence time $T_S$ is about 10 seconds or less and preferably less than 8 seconds; the first predetermined sample travel time $T_{pred1}$ is about 50 to about 500 milliseconds and preferably about 100 milliseconds; the second predetermined sample travel time $T_{pred2}$ is less than one second; the predetermined difference $D_{pred}$ is about 10% to about 30%; and "significant output signal" means about 10% of any of the thresholds TH1, TH2, or TH3.

Moreover, while the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

The invention claimed is:

1. A method of determining a sample fill error in an analyte test strip having at least two electrodes spaced apart along a fill passage disposed on a substrate that extends from at least a first opening to a second opening, the method comprising the steps of:

applying a signal to first and second electrodes of the at least two electrodes;

depositing a fluid sample into one of the first and second openings;

monitoring the first and second electrodes for output signals indicative of an electrochemical reaction with the sample; and in the event the first electrode or the second electrode outputs a signal before the other of the first and second electrodes then monitoring the other of the first and second electrodes for a signal output within a predetermined time period else reporting a fill error when the signal output of the other electrode is after the predetermined time period.

2. The method of claim 1, further comprising:

measuring a signal from the second electrode during a sampling interval of a test sequence time;

comparing a magnitude of the signal from the second electrode with magnitude of the signal from the first electrode; and reporting an error if the magnitude of the signal from the second electrode is different by a predetermined percent differential from the magnitude of the signal from the first electrode otherwise summing the magnitudes of the signals and calculating an analyte concentration based on the summed magnitudes.

3. The method of claim 1, further comprising:

measuring a signal from the first electrode during a sampling interval of a test sequence time;

comparing a magnitude of the signal from the first electrode with magnitude of the signal from the second electrode; and reporting an error if the magnitude of the signal from the first electrode is different by a predetermined percent differential from the magnitude of the signal from the second electrode otherwise summing the magnitudes of the signals and calculating an analyte concentration based on the summed magnitudes.

4. The method of one of claim 2 or claim 3, in which the predetermined percent differential comprises any value from about 30% to 10%.

5. A method of determining a sample fill error in an analyte test strip having at least first, second, fourth, and fifth electrodes spaced apart along a fill passage disposed on a substrate that extends from at least a first opening to a second opening, the method comprising the steps of:

applying a signal to the first, second, third, and fourth electrodes;

depositing a fluid sample into one of the first and second openings;

monitoring the first through fourth electrodes for a signal output;

in the event the first electrode outputs a signal greater than a first threshold before one of the third or fourth electrodes outputs a signal greater than a second threshold then:

sampling the signal from the first electrode and measuring the second, third and fourth electrodes for a signal output from the second electrode greater than the first threshold and a signal output from at least one of the third and fourth electrodes greater than the second threshold within a first predetermined time period otherwise reporting a fill error when the signal output from at least one of the third and fourth electrodes is after the first predetermined time period.

6. The method of claim 5, further comprising the steps of:

in the event one of or both of the third and fourth electrodes output a signal greater than the third threshold before one of the first and second electrodes outputs a signal greater than the first threshold then:

determining whether the first electrode outputs a signal greater than the first threshold before the second electrode and reporting an error if true, otherwise determining whether the second electrode outputs a signal greater than the first threshold before the first electrode and if true monitoring the first electrode to determine whether the first electrode outputs a signal greater than the first threshold within a second predetermined time period, and in the event the first electrode fails to outputs a signal greater than the first threshold within the second time period, reporting an error.

7. The method of claim 6, further comprising detecting whether a signal output from the second electrode is greater than a third threshold before a signal output from any one of the first, third and fourth electrodes and if the detecting is true, reporting an error.

8. The method of claim 6, in which the measuring of the second, third and fourth electrodes further comprises comparing a magnitude of the signal from the second electrode with the first electrode and outputting an error whenever a difference in magnitude between the signal of the first electrode and the signal of the second electrode is greater than a predetermined percentage.

9. The method of claim 6, in which the determining further includes comparing a magnitude of the signal from the second electrode with the first electrode and outputting an error whenever a difference in magnitude between the signal of the first electrode and the signal of the second electrode is greater than a predetermined percentage.

10. The method of claim 8, in which the predetermined percent differential comprises any value from about 30% to 10%.

11. The method of one of claim 1 or claim 5, in which the analyte test strip further includes a fifth electrode connected to one of the first, second, third and fourth electrodes.

12. The method of claim 11, in which a reagent is disposed on the first and second electrodes and no reagent on the third and fourth electrodes.

13. The method of claim 12, in which a reference electrode is disposed proximate the first and second electrodes.

14. The method of claim 12, further comprising a fifth electrode disposed proximate the opening closest to one of the third and fourth electrodes.

15. The method of claim 13, in which a reference electrode is disposed between the first and second electrodes.

16. The method of claim 14, in which the reference electrode is connected to the fifth electrode disposed proximate the opening of the passage closest to one of the third and fourth electrodes.

17. A method of determining a sample fill direction for an analyte test strip having at least two electrodes spaced apart along a fill passage disposed on a substrate that extends from at least a first opening to a second opening, the method comprising the steps of:

applying a signal to first and second electrodes of the at least two electrodes;

depositing a fluid sample into one of the first and second openings;

monitoring the first and second electrodes for output signals indicative of an electrochemical reaction;

in the event the first electrode outputs a signal greater than a first predetermined threshold before the second electrodes, storing in memory an indication that a direction of the movement of the sample is in a first direction; and in the event the second electrode outputs a signal greater than a second predetermined threshold before the first electrode, storing in memory an indication that a direction of the movement of the sample is in a second direction.

18. A method of determining a sample fill direction for an analyte test strip having at least first, second, fourth, and fifth electrodes spaced apart along a fill passage disposed on a substrate that extends from at least a first opening to a second opening such that a sample can move from the first opening toward the second opening or from the second opening toward the first opening, the method comprising the steps of:
   applying a signal to the first, second, third, and fourth electrodes;
   depositing a fluid sample into one of the first and second openings;
   monitoring the first through fourth electrodes for a signal output;
   in the event the first electrode outputs a signal greater than a first threshold before one of the third or fourth electrodes outputs a signal greater than a third threshold then:
      selecting a first measurement based on output signals from each of the first and second electrodes before a second measurement based on output signals from the third and fourth electrodes; and
   in the event the third and fourth electrodes output a signal greater than a second threshold and before any output signal from one of the first and second electrodes then:
      selecting the second measurement based on output signals from the third and fourth electrodes before the first measurement based on output signals from each of the first and second electrodes.

19. A system comprising:
   a test strip, the test strip including:
      a substrate having at least first, second third, fourth, and fifth electrodes disposed in a passage extending between a first opening and a second opening to permit fluid sample to flow into one or more of the openings; and
   a test meter including:
      a housing;
      a test strip port connector configured to connect to the respective electrode connectors of the test strip; and
      a microprocessor in electrical communication with the test strip port connector to apply electrical signals or sense electrical signals from the plurality of electrodes during a test sequence, wherein the microprocessor is configured to:
      (a) apply a signal to the first, second, third, and fourth electrodes;
      (b) monitor the first through fourth electrodes for a signal output representative of a deposition of fluid sample onto the test strip;
      (c) in the event the first electrode outputs a signal greater than a first threshold before one of the third or fourth electrodes outputs a signal greater than a second threshold then:
         (i) sample the signal from the first electrode and
         (ii) measure the second, third and fourth electrodes for a signal output from the second electrode greater than the first threshold and a signal output from at least one of the third and fourth electrodes greater than the second threshold within a first predetermined time period otherwise report a fill error when the signal output from at least one of the third and fourth electrodes is after the first predetermined time period;
      (d) in the event one of or both of the third and fourth electrodes output a signal greater than the third threshold before one of the first and second electrodes outputs a signal greater than the first threshold then:
         (i) determine whether the first electrode outputs a signal greater than the first threshold before the second electrode and report an error if true,
         (ii) otherwise determine whether the second electrode outputs a signal greater than the first threshold before the first electrode and if true monitor the first electrode to determine whether the first electrode outputs a signal greater than the first threshold within a second predetermined time period, and
      (e) in the event the first electrode fails to outputs a signal greater than the first threshold within the second time period, report an error.

* * * * *